United States Patent
Stone et al.

[19]

[11] Patent Number: 5,843,027
[45] Date of Patent: Dec. 1, 1998

[54] BALLOON SHEATH

[75] Inventors: Gregg Stone, Los Altos Hills; Michael Crocker, Mission Viejo; Robert J. Elicker, Rancho Santa Margarita; Lynn Shimada, Irvine, all of Calif.

[73] Assignee: Cardiovascular Dynamics, Inc., Irvine, Calif.

[21] Appl. No.: 767,107

[22] Filed: Dec. 4, 1996

[51] Int. Cl.$^6$ .................................................. A61M 31/00
[52] U.S. Cl. ................................ 604/53; 604/49; 604/96; 606/194
[58] Field of Search ............................. 604/96; 606/108, 606/192, 194

[56] References Cited

U.S. PATENT DOCUMENTS

| | | |
|---|---|---|
| 4,790,315 | 12/1988 | Mueller, Jr. et al. . |
| 4,922,905 | 5/1990 | Strecker . |
| 4,950,227 | 8/1990 | Savin et al. . |
| 5,116,318 | 5/1992 | Hillstead . |
| 5,192,297 | 3/1993 | Hull . |
| 5,195,971 | 3/1993 | Sirhan . |
| 5,211,654 | 5/1993 | Kaltenbach . |
| 5,226,889 | 7/1993 | Sheiban . |
| 5,242,399 | 9/1993 | Lau et al. . |
| 5,257,974 | 11/1993 | Cox ........................................... 604/96 |
| 5,295,962 | 3/1994 | Crocker et al. . |
| 5,342,305 | 8/1994 | Shonk . |
| 5,344,402 | 9/1994 | Crocker . |
| 5,368,566 | 11/1994 | Crocker . |
| 5,409,495 | 4/1995 | Osborn . |
| 5,415,635 | 5/1995 | Bagaoisan et al. . |
| 5,421,826 | 6/1995 | Crocker et al. . |
| 5,439,446 | 8/1995 | Barry . |
| 5,453,090 | 9/1995 | Martinez et al. . |

FOREIGN PATENT DOCUMENTS 0 347 023 A2  12/1989  European Pat. Off. .
WO 95/09667  4/1995  WIPO .

*Primary Examiner*—Wynn Wood Coggins
*Assistant Examiner*—Deborah Blyveis
*Attorney, Agent, or Firm*—Knobbe, Martens, Olson & Bear, LLP

[57] ABSTRACT

Disclosed is a tuvular sheath which is adapted to fit coaxially over an inflatable balloon. The sheath functions to alter the expansion characteristics of the balloon. In one preferred embodiment, the sheath converts the inflation profile of a dilatation balloon from a compliant mode to a noncompliant mode. Advantageously, the balloon sheath may be used in stent placement procedures, to accurately size the stent within a body lumen, while providing protection against balloon rupture. In one embodiment, the balloon sheath comprises a two-layered tubular structure, with an outer elastic layer surrounding an inner inelastic layer. Also disclosed are methods of altering the expansion characteristics of a balloon using the balloon sheath.

7 Claims, 3 Drawing Sheets

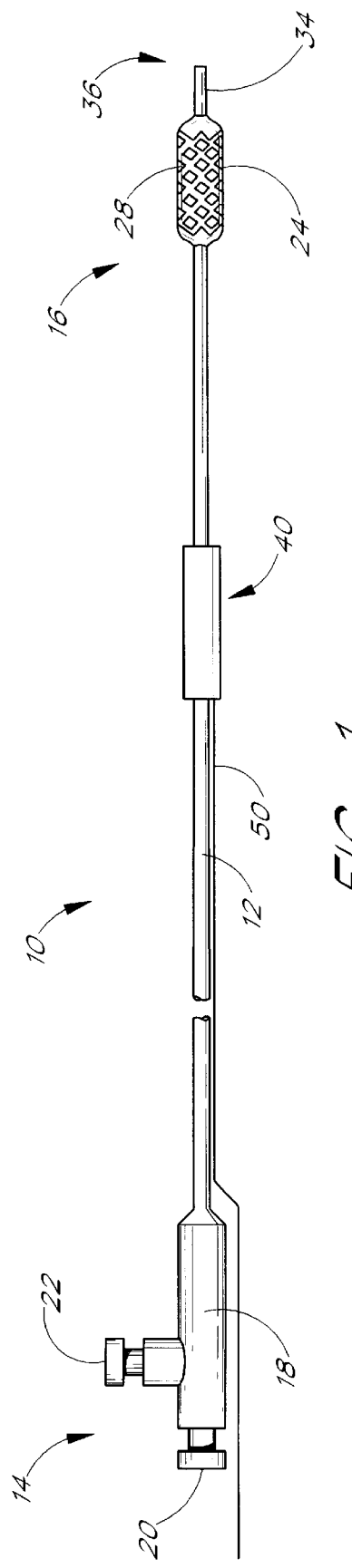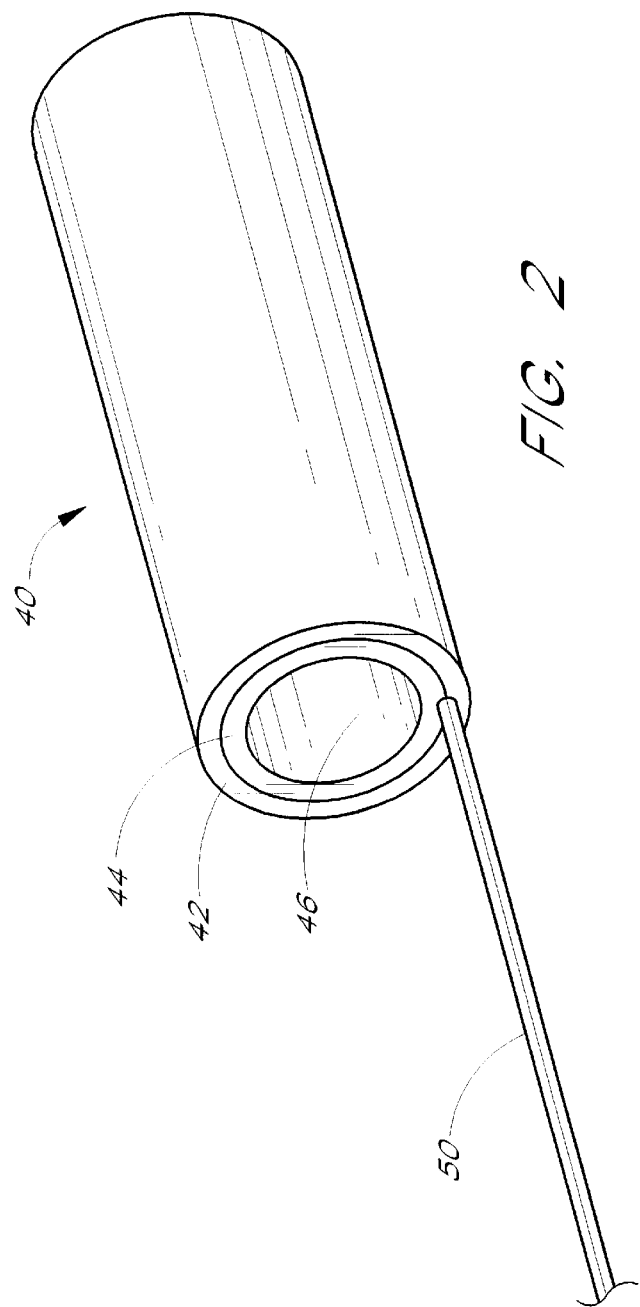

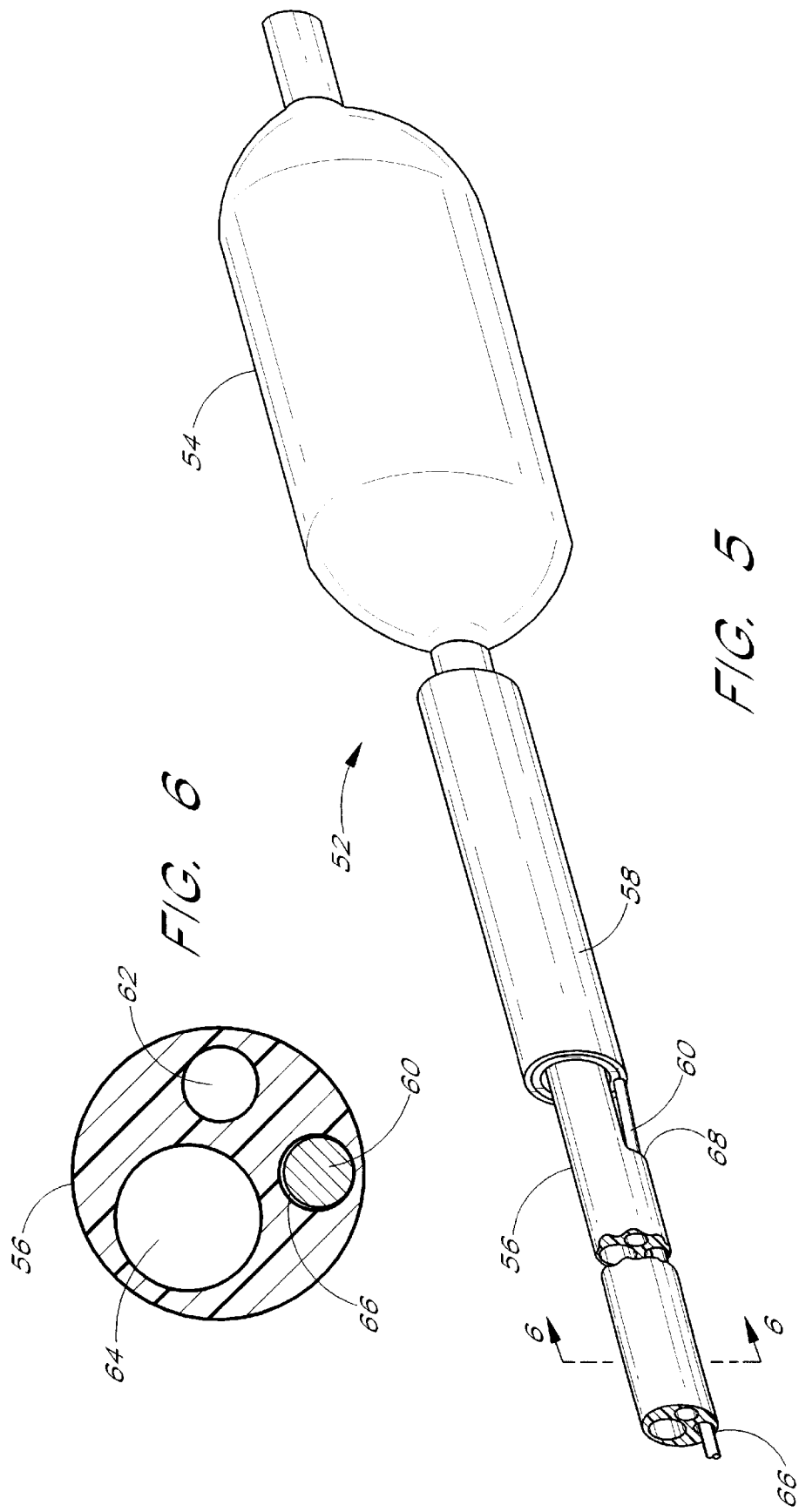

BALLOON SHEATH

BACKGROUND OF THE INVENTION

The present invention relates to medical balloon catheters and, in particular, to a sheath which may be placed over a dilatation balloon to modify the expansion characteristics of the balloon.

A wide variety of catheters have been developed in the prior art for percutaneous transluminal coronary or peripheral vascular applications. For example, balloon dilatation catheters for performing percutaneous transluminal coronary angioplasty ("PTCA") are well known in the art.

In general, PTCA is one procedure for treating a narrowed region in an artery, which, in one form, uses a catheter having an expandable balloon thereon. The catheter is percutaneously inserted such as into a femoral artery, and advanced transluminally until the dilatation balloon is positioned within the restricted portion of the lumen. The balloon is thereafter inflated to radially outwardly displace the obstruction to restore some or all of the original interior diameter of the lumen.

Intravascular stents are occasionally used following balloon angioplasty dilatation procedures to possibly reduce the occurrence of restenosis. Stents are expandable tubular supports for maintaining patency of the lumen following balloon dilatation or other treatment protocols. See, for example, U.S. Pat. No. 4,776,337 to Palmaz.

Intravascular stents are typically deployed by a catheter having a stent prepositioned over an expandable balloon. The clinician percutaneously inserts the catheter and transluminally advances it to position the stent at the appropriate vascular treatment site. The balloon is then inflated to enlarge the stent against the arterial wall.

When a stent is placed within a lumen, it is important that it be accurately "sized" with respect to the inside diameter of the lumen. The stent must generally be radially expanded to a sufficient diameter that the outer surface of the stent firmly contacts the interior lumen wall, thereby providing support to the lumen. It is also desirable to expand the stent such that the inside diameter of the stent approximates the native lumen diameter to minimize stent obstruction of fluid flow through the lumen. However, excessive radial expansion of the stent is undesirable, and may result in damage to the vessel wall.

Conventional stent deployment catheters such as the SDS available from Johnson & Johnson are often provided with balloons which exhibit compliant expansion characteristics. A compliant balloon tends to exhibit an increasing radial diameter with increasing inflation pressure, until the balloon burst pressure or rated maximum is reached. Because of this expansion profile, compliant balloons may not provide the optimum degree of control desired for stent implantation or sizing procedures. Indeed, to reduce the risk of overexpansion of a stent, clinicians often use catheters with compliant balloons only to partially expand a stent, and then remove that catheter and insert a second less-compliant stent sizing catheter to appropriately size the implanted stent to the lumen.

Conventional noncompliant stent sizing balloons present problems under certain circumstances as well. Many noncompliant balloons used for stent sizing are made of thin-walled materials, such as polyethylene terephthalate ("PET"). When catheters with these types of balloons are used to size metallic-mesh stents, there exists an increased risk of perforation of the balloon by a stent strut. Moreover, rupture of a stent sizing balloon under high pressures may lead to arterial trauma.

Thus, there remains a need for a device which can be used in conjunction with stent implantation or sizing balloons, to improve control, increase burst pressure and also to reduce the risk of perforation of the balloon by the stent.

SUMMARY OF THE INVENTION

The present invention is directed toward a sheath which can be used with a variety of conventional balloon catheters to enable those balloons to properly size a stent to a body lumen, while also protecting the balloons from perforation by a stent.

In accordance with one aspect of the present invention, the balloon sheath has an inner tubular sleeve formed of a relatively noncompliant material. An outer tubular sleeve formed of a relatively elastic material surrounds at least a portion and preferably all of the inner sleeve. The sheath is adapted to be positioned concentrically over a dilatation balloon, such as a conventional compliant balloon. When inflation media is introduced into the balloon, the balloon is constrained to a relatively noncompliant inflation profile by the noncompliant layer on the sheath, while the elastic layer reduces the risk of perforation.

In one preferred embodiment, the inner sleeve comprises polyethylene terephthalate.

Additionally, the balloon sheath may have a push wire attached to and extending from the proximal end of the sheath. The push wire extends proximally to a point outside of the patient, so that the sheath can be advanced proximally or distally while the balloon is in position at the treatment site. In one embodiment, the push wire extends proximally from the sheath alongside the outside of the catheter body. In another embodiment, the push wire extends proximally through a lumen within the catheter body.

In accordance with another aspect of the present invention, there is provided a method of sizing a stent to an interior body lumen. The first step of the method is to provide a tubular balloon sheath. In one embodiment, the sheath has an outer sleeve of a first, relatively elastic material and an inner sleeve of a second, relatively inelastic material. The balloon sheath is then positioned coaxially about a balloon on a balloon catheter. The balloon and sheath are positioned within a previously deployed tubular stent. The balloon is then inflated inside the stent, so that the sheath constrains the balloon to a substantially noncompliant inflation profile having a preselected diameter. Optimally, the substantially noncompliant inflation profile provides a sufficient radial diameter to expand the stent to an appropriate implanted diameter without causing excessive trauma to the lumen.

In accordance with a another aspect of the present invention, there is provided a method of altering the expansion characteristics of a dilatation balloon. The dilatation balloon is of the type, which when fully inflated, has a first inflation diameter at a reference pressure. A balloon sheath is placed over the deflated dilatation balloon. The balloon sheath is formed in part of a relatively inelastic material. When the dilatation balloon is inflated to the reference pressure, the balloon sheath restricts expansion of the dilatation balloon to a controlled inflation diameter which is smaller than the first inflation diameter.

In another aspect of the present invention, the balloon sheath may be used to increase the inflation pressure handling characteristics of a dilatation balloon. Dilatation balloons are normally rated to have a characteristic burst pressure. By covering the dilatation balloon with the balloon sheath of the present invention, structural support is provided to the dilatation balloon, enabling it to withstand pressures in excess of its previously rated burst pressure.

BRIEF DESCRIPTION OF THE DRAWINGS

FIG. 1 is a side elevational view of a balloon dilatation catheter incorporating the balloon sheath of the present invention.

FIG. 2 is a perspective schematic view of the balloon sheath of the present invention.

FIG. 5 is a perspective view of a balloon sheath on a catheter having an internal push wire.

FIG. 6 is a cross section through the line 6—6 in FIG. 5.

DETAILED DESCRIPTION OF THE PREFERRED EMBODIMENT

Figure 3:
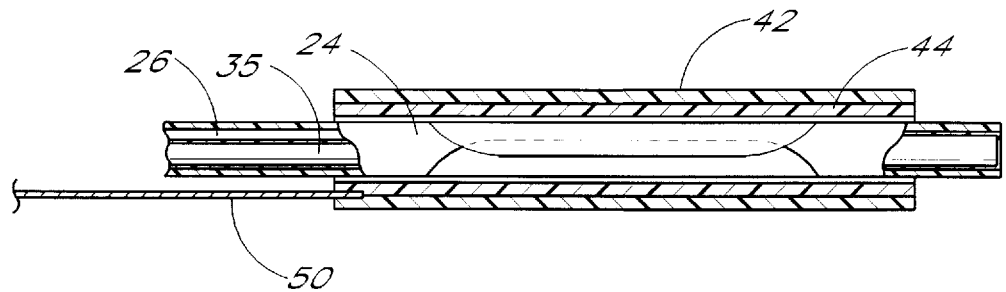
FIG. 3 is a cross-sectional view of the balloon sheath positioned over a deflated dilatation balloon.

Referring to FIG. 1, there is depicted a stent deployment and/or sizing catheter 10 incorporating the balloon sheath of the present invention. Although illustrated in the context of a simple over the wire vascular balloon dilatation catheter, having a single inflation lumen and a single guidewire lumen, it is to be understood that the balloon sheath of the present invention can be readily adapted to essentially any balloon catheter regardless of what additional functions or structures the catheter may have.

For example, the present inventors contemplate the use of the balloon sheath in catheters having balloon dilatation and blood perfusion capabilities, as well as other combinations of functional features which may be desirable in a particular intended application. Moreover, the balloon sheath of the present invention may be used to dilate vessels and/or size stents in any of a variety of body lumen, such as in urethral, ureteral, bile duct, venous, and arterial stent placement applications. The manner of adapting the balloon sheath of the present invention to catheters having these various functionalities or intended uses will become readily apparent to those of skill in the art in view of the description which follows.

Catheter 10 generally comprises an elongate tubular flexible body 12 extending between a proximal control end 14 and a distal functional end 16. The length of the tubular body 12 depends upon the desired application. For example, lengths in the area of from about 120 centimeters to about 140 centimeters are typical for use in coronary stent placement applications. In general, tubular body 12 will have a generally circular cross-sectional configuration with an external diameter within the range of from about 0.023 inches to 0.065 inches for most cardiovascular applications. Alternatively, a generally triangular cross-sectional configuration can also be used, depending upon the number of lumen in the catheter, with the maximum base to apex distance also generally within the range of from about 0.023 inches to about 0.065 inches. Other noncircular catheter configurations, such as rectangular or oval, may also be used with the balloon sheath of the present invention.

In peripheral vascular stent placement applications, tubular body 12 will typically have an outside diameter within the range of from about 0.039 inches to about 0.065 inches. In coronary vascular stent placement or sizing applications, tubular body 12 will typically have an outside diameter within the range of from about 0.030 inches to about 0.045 inches.

Stent placement of sizing catheters having diameters outside the preferred range may also be used with the balloon sheath of present invention, as described below, provided that the functional consequences of the diameter are acceptable for the specified intended purpose of the catheter. For example, the lower limit of the diameter for tubular body 12 in a given application will be a function of the number of fluid or other functional lumen contained in the catheter, together with the acceptable flow rate of dilatation fluid or other fluid to be delivered through the catheter. Catheters having larger tubular body diameters generally have sufficient internal flow properties and structural integrity, but reduce perfusion in the artery in which the catheter is placed and cannot reach small diameter vessels. In addition, increased diameter catheter bodies tend to exhibit reduced flexibility, which can be disadvantageous in stent placement applications in a remote vascular location.

Tubular body 12 must have sufficient structural integrity (i.e., "pushability") to permit the catheter to be advanced to distal arterial locations without buckling or undesirable bending of tubular body 12. The ability of tubular body 12 to transmit torque may also be desirable, such as in those embodiments where it may be desirable to rotate the tubular body 12 after insertion.

The proximal end 14 of the stent sizing catheter 10 is generally provided with a manifold 18 having a plurality of access ports, as is known in the art. Generally, manifold 18 is provided with a guidewire port 20 in an over-the-wire embodiment and a balloon inflation port 22. Guidewire port 20 is in communication with a guidewire lumen 35, which extends axially along the length of catheter 10. An opening 38 is provided at the distal end of the catheter for introduction of the proximal end of the guidewire (not illustrated) into guidewire lumen 35. The proximal guidewire port 20 may be eliminated from manifold 18 in a rapid-exchange or "monorail" embodiment, in which embodiment the proximal opening of the guidewire lumen 35 is positioned along the side of tubular body 12. The proximal guidewire access port in a rapid exchange embodiment is typically within about 20 cm from the distal end of the catheter.

Inflation port 22 is in fluid communication with the balloon 24 by way of an axially extending inflation lumen 26.

Additional access ports may be provided on manifold 18 as needed, depending upon the functional capabilities of the catheter. For example, a push wire access port can be provided in an embodiment having an axially moveable sheath with an internal push wire as will be discussed. See FIG. 5.

The distal end 16 of the catheter is preferably provided with an a traumatic distal tip 36, as is known in the art. Preferably, one or more radio opaque markers are also provided to facilitate positioning of the catheter. Suitable marker bands can be produced from any of a variety of materials, including platinum, gold, and tungsten\rhenium alloy.

The distal end 16 of the catheter 10 is additionally provided with an inflatable balloon 24, having a stent 28 mounted thereon, illustrated schematically in FIG. 1. Inflatable balloon 24 may be made from any of a variety of materials known by those of skill in the art to be suitable for dilatation balloon manufacture. For example, inflation balloon 24 may be formed of materials imparting relatively compliant expansion characteristics such as conventionally treated polyethylenes. When compliant materials are used, once fully inflated, the diameter of balloon 24 will tend to increase in response to further increases in inflation pressure, until an elastic limit or the burst pressure of inflation balloon 24 is reached.

Alternatively, inflation balloon 24 may be formed of materials imparting relatively noncompliant expansion characteristics such as conventional polyethylene terephthalate (PET) formulations. Balloons formed of noncompliant materials such as PET generally inflate to a predetermined inflation diameter, which is substantially maintained upon increasing inflation pressure, until the burst pressure of the balloon is reached.

Referring to FIGS. 1 and 2, there is illustrated one embodiment of the balloon sheath 40 of the present invention. Balloon sheath 40 comprises a tubular body which is adapted to be positioned coaxially about any of a variety of conventional inflation balloons. Sheath 40 can be positioned over the balloons of catheters currently on the market to improve the predictability of the inflated diameter at preselected inflation pressures. In particular, the sheath can limit compliant growth of the underlying balloon in response to increased inflation pressure, thereby producing an essentially non-compliant balloon assembly. The sheath 40 can also improve the pressure handling characteristics of the underlying balloon by elevating the burst pressure of the balloon. The sheath 40 can be positioned over a balloon and secured in place such as by adhesives, thermal bonding and the like, or can be axially moveable with respect to the balloon as will be discussed.

In the illustrated embodiment, balloon sheath 40 has a two layer structure, with an outer sleeve 42 and inner sleeve 44. A lumen 46 extending through balloon sheath 40 is defined by the interior surface of inner sleeve 44. Alternatively, a single layer sheath, or a sheath having three or more layers can also be desirable, depending upon the intended application.

Sheath 40 is constructed to be radially outwardly expandable from a first, insertion diameter to a second, enlarged diameter such as for dilating a stenosis or sizing a stent. "Expansion" may occur by stretching the material of the sheath, or by unfolding or unwrinkling the sheath, or both, depending upon its construction.

Preferably, the sheath 40 is provided with one or more radiopaque markers such as a radiopaque marker band at the proximal and/or distal regions of the sheath. In a two layer sheath, the marker band(s) may be sandwiched between the two layers. Marker bands will enable visualization of the axial position of the sheath relative to other radiopaque structures, such as a stent or an inflation balloon filled with contrast media.

In one preferred embodiment, outer sleeve 42 is formed of a resilient or elastic material which tends to contract back to a preselected relaxed size after being expanded. Outer sleeve 42 may be formed from any of a wide variety of materials, such as latex, silicone, polyurethane elastomer, C-Flex, Tecoflex, nylon elastomers (PEBAX), as well as other materials known to those of skill in the art.

In general, selection of material for sleeve 42 will be guided by the intended application of sheath 40. For example, in applications where metal-mesh stents will be placed or sized, it is preferable that sleeve 42 be made of a relatively puncture-resistant elastic material, or of sufficient thickness, so as to provide an adequate protective covering to prevent puncture of balloon 24 by stent struts.

Inner sleeve 44 is preferably made from a material which is relatively inelastic, and preferably a material which is substantially noncompliant at typical balloon inflation pressures. The material of inner sleeve 44 should also be resistant to bursting at the contemplated inflation pressure of the intended inflation balloon. A variety of inelastic materials having these properties may be used to form sleeve 44, such as PET and nylon, in addition to other materials which can be determined by those of skill in the art.

The dimensions of the sheath can be varied as appropriate to fit the intended balloon catheter and desired inflation characteristics. In one embodiment, the sheath has an axial length of about 6 cm, and a total wall thickness of about 0.004" in the relaxed state. The relaxed outside diameter of the unmounted sheath is about 0.065" and the outside diameter at an inflation pressure of 60 psi is about 3 mm. The inner PET layer has a thickness of about 0.0003" and the outer urethane layer has a thickness of about 0.004".

As a consequence of the structure described above, the outer sleeve 42 will tend to elastically constrict to its first, relaxed diameter. The inner sleeve 44 will be forced to fold or wrinkle to accommodate the radial reduction of outer sleeve 42. Expansion of a balloon within sheath 40 causes the inner sleeve to unfold to its preset maximum diameter while elastically expanding the outer sleeve 42 to a corresponding diameter. Thus, sleeve 44 can be used to set a precise inflated maximum diameter at a preselected pressure and sleeve 42 can improve puncture resistance and assist during deflation and placement and removal steps by minimizing winging of the sleeve 44. In applications where these latter features are unnecessary, the order of inner sleeve 44 and outer sleeve 42 can be reversed, or either the inner or the outer sleeve can be eliminated.

In one preferred embodiment, outer sleeve 42 and inner sleeve 44 are bonded together. Sleeve bonding may be performed by any of a variety of means known to those of skill in the art, such as heat sealing or by use of adhesives. Moreover, the extent of the bond between the two sleeves may be varied considerably and still form the balloon sheath of the present invention. For example, in some embodiments, it may be desirable to bond the entire outer surface of inner sleeve 44 to the inner surface of outer sleeve 42. Alternatively, the two sleeves may be bonded together along only portions of their surfaces, as for example, along the inner and outer circumferences near the edges of the two sleeves or at discrete spot welds.

The two-layer embodiment of the sheath described above can be manufactured by bonding the inner and outer sleeves proximal and distal to the region of expansion by a suitable adhesive.

In the embodiment illustrated in FIGS. 1 and 2, balloon sheath 40 has an attached push wire 50 extending from its proximal end. Advantageously, push wire 50 facilitates axial movement of balloon sheath 40 along tubular body 12 and balloon 24, so that balloon sheath 40 may, for example, be positioned proximally of the balloon 24 along the catheter shaft during catheter placement, and then advanced distally over deflated balloon 24 and within a partially expanded stent prior to stent sizing. Push wire 50 may also be used to retract balloon sheath 40 after a stent sizing procedure, to ensure removal of sheath 40 along with the catheter from the blood vessel following deflation of balloon 24. Although the sleeve can for some uses be secured to the balloon permanently thereby reducing the need for a push wire, the ability to axially advance the sleeve over the balloon following placement of the balloon can be advantageous in a number of applications.

Push wire 50 may be attached to sheath 40 in a variety of ways. For example, push wire 50 may be attached to the proximal end of either outer sleeve 42 or inner sleeve 44 by molding the respective sleeve thereon during manufacture. Alternately, push wire 50 may be adhesively bonded to either sleeve. In another embodiment, push wire 50 may be attached to balloon sheath 50 by inserting push wire 50 between outer sleeve 42 and inner sleeve 44, and then bonding the two sleeves together to secure push wire 50 therebetween.

Push wire 50 may be formed of any medical grade material with sufficient structural integrity to permit sheath 40 to be advanced or retracted over balloon 24 and along tubular body 12. Presently preferred materials for the manufacture of push wire 50 include stainless steel and nitinol. In one embodiment, push wire 50 comprises stainless steel and has an outside diameter of about 0.016".

Referring to FIGS. 5 and 6, there is disclosed an internal push wire embodiment of the present invention. A balloon dilatation catheter 52 is provided with an inflatable balloon 54 on the distal end of an elongate flexible tubular body 56. An axially movable sheath 58 is positioned on the tubular body 56 proximally of inflatable balloon 54. A push wire 60 is secured to the tubular sleeve 58 and extends proximally throughout the length of the catheter. In this embodiment, at least a portion of push wire 60 is axially movably disposed within an elongate push wire lumen 66.

Push wire lumen 66 is provided with a distal aperture 68, through which push wire 60 can exit the catheter body. Aperture 68 is positioned proximally of the balloon 54 by a sufficient distance to permit the tubular sheath 58 to be withdrawn proximally of the balloon 54. For example, in a balloon catheter having a 2 cm long dilatation balloon, the tubular sheath 58 will be approximately 3 cm long, and the aperture 68 will be positioned within the range of from about 3.5 cm to about 6 cm proximally of the proximal end of the balloon 54.

Referring to FIG. 6, the catheter body 56 is provided with a push wire lumen 66 as has been discussed, as well as an inflation lumen 62 and a guidewire lumen 64 as is known in the art. As with previous embodiments herein, additional lumen may be provided as needed, depending upon the desired functionality of the catheter. Alternatively, the guidewire lumen 64, may be eliminated from proximal portions of the catheter such as in a rapid exchange embodiment.

Whether the push wire extends proximally internally or externally to the catheter body, the push wire embodiment of the present invention permits a variety of dilatation, stent implantation and stent sizing methods. For example, in accordance with one aspect of the method of the present invention, a tubular sheath is mounted on a dilatation balloon. An expandable implantable stent is coaxially mounted on the tubular sheath either at the point of manufacture or at the clinical site. The assembly may thereafter be positioned within a treatment site, and the balloon inflated to expand the stent. The tubular sheath both improves the predictability of the inflated diameter of the balloon, as well as increases the pressure capacity of the balloon. This method can be accomplished with a balloon sheath of the present invention with or without a push (or safety) wire.

In accordance with another aspect of the present invention, a tubular sheath having a push wire attached thereto is mounted on a balloon catheter, either at the point of manufacture or at the clinical site. The sheath is positioned initially on the catheter shaft proximally of the balloon. An expandable stent may optionally be positioned over the balloon. The assembly is percutaneously inserted and transluminally advanced to a treatment site in a body lumen. The balloon is thereafter inflated to enlarge the stent at the treatment site. The balloon is then deflated by aspiration of inflation media, and the tubular sheath is thereafter advanced distally by distal pressure on the push wire, so that the tubular sheath is positioned over the deflated balloon. The balloon may thereafter be reinflated, optionally to a higher pressure than the pressure used to implant the stent, to size the stent to the body lumen.

In accordance with a further aspect of the method of the present invention, a tubular sheath having a proximally extending push wire 50 is positioned on a balloon dilatation catheter proximally of the balloon. The catheter may thereafter be transluminally positioned such that the balloon is within a treatment site, and the balloon dilated to predilate the stenosis. The balloon is thereafter deflated, and the tubular sheath advanced distally over the balloon. The balloon may then be inflated to a higher pressure, to produce a predetermined inflation diameter. The foregoing method may be utilized either to size a previously implanted stent, or to dilate a stenosis without the use of a stent.

In certain circumstances, it may be desirable to eliminate push wire 50 and attach sheath 40 directly to catheter 10 over balloon 24. Attachment of the sheath to the balloon in an embodiment without a push wire can be accomplished at the original point of manufacture, or as a "retrofit" to improve or alter the characteristics of a commercially available catheter. Sheath 40 can have an axial length of substantially the same length or less than the length of the balloon. In these embodiments, the sheath is preferably bonded directly to the balloon. Bonding may be achieved by any manner known to those of skill in the art, such as heat sealing, spot welding, solvent bonding or by use of adhesives. The weld or other adhesion points between sheath 40 and balloon 24 may be varied as desired.

Alternatively, the sheath 40 can have an axial length of greater than the axial length of the underlying balloon. Such sheaths can be secured to the catheter shaft at the proximal side and/or the distal side of the balloon. Bonding of the sheath to the catheter shaft can be accomplished by any of the techniques discussed above, as well as by shrinking proximal and distal necks on the sheath such as by the application of heat.

Figure 4:
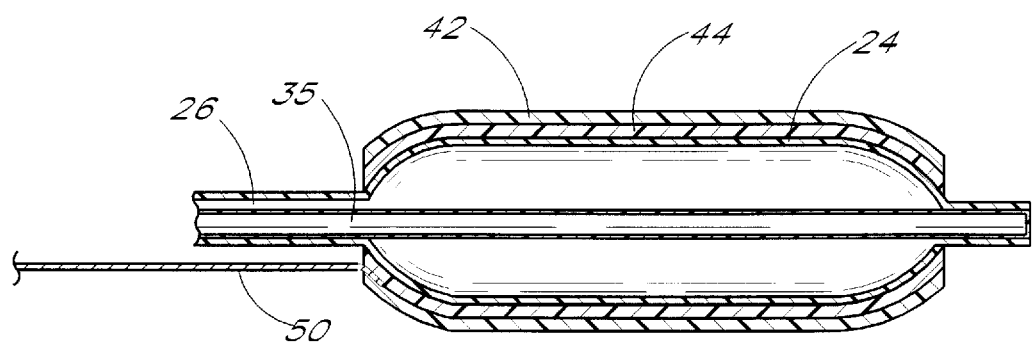
FIG. 4 is a cross-sectional view of the balloon sheath positioned over an expanded dilatation balloon.

The balloon expansion-altering and protection properties of balloon sheath 40 are illustrated schematically in FIGS. 3 and 4. Considering an embodiment in which balloon 24 is of the compliant variety, as inflation media is introduced into balloon 24 though inflation lumen 26, the radial diameter of balloon 24 will increase from that shown in FIG. 3 to the diameter of FIG. 4. As seen in FIG. 4, the outer surface of balloon 24 will be in substantially complete contact with noncompliant inner sleeve 44 of sheath 40 as balloon 24 fully inflates. As inflation pressure increases beyond the point of full inflation of balloon 24, inner sleeve 44 restrains further expansion of balloon 24, so that balloon 24 has a substantially constant expanded diameter rating at a increased pressures. Thus, in effect, sleeve 44 serves to convert the expansion characteristics of balloon 24 from a compliant mode to a noncompliant mode. Moreover, the added structural support of sleeve 44 in contact with balloon 24 improves the pressure handling characteristics underlying balloon 24, permitting balloon 24 to be exposed to higher inflation pressures without bursting.

Outer sleeve 42 surrounds inner sleeve 44, and being formed of an elastic material, will expand in conjunction with inner sleeve 44. A stent (not shown), may be positioned over outer sleeve 42 prior to catheter insertion, or sheath 40 and balloon 24 may be inserted within a partially expanded stent already positioned within a lumen. As balloon 24 expands, outer sleeve 42 will also expand and contact the stent, thereby increasing the stent's radial diameter, which will result in the sizing of the stent to the lumen. Being formed of a material resistant to puncture, outer sleeve 42 also tends to protect balloon 24 and inner sleeve 44 from perforation by stent struts. In addition, because of its elastic nature, sleeve 42 will also exert a compressive force on balloon 24 as it is deflated. This will facilitate balloon collapsing on deflation, to minimize the profile of the deflated balloon prior to catheter withdrawal and prevent "winging out" of the balloon. Advantageously, this minimizes the risk that the newly implanted stent will be dislodged as balloon 24 and sheath 40 are removed from the implantation site.

Furthermore, should balloon 24 rupture during a high pressure stent implantation procedure, the two sleeves of sheath 40 may prevent or minimize any trauma to the lumen. Moreover, the compressive nature of sleeve 42 should ensure removal of balloon material without stent entanglement.

Optimally, balloon sheath 40 is selected so that the inflation diameter of the sheath-covered balloon is appropriate for the particular stent placement application. Thus, it is contemplated that the present invention can be used to adapt a particular catheter to a number of different stent placement and sizing applications, simply by selecting an appropriate sheath from a number of sheaths each having a unique inflated diameter rating at a reference pressure. As will be appreciated by those of skill in the art, varying the materials and manufacturing processes used to form inner sleeve 44 allows creation of sheaths with variety of non-compliant expansion profiles.

Any of the foregoing methods can alternatively be accomplished using a single layer sheath, comprising any of the materials disclosed herein, depending upon the desired functional characteristics of the balloon and sheath assembly.

It will be appreciated that certain variations of the present invention may suggest themselves to those skilled in the art. The foregoing detailed description is to be clearly understood as given by way of illustration, the spirit and scope of this invention being limited solely by the appended claims.

What is claimed is:

1. A method of sizing a stent to an interior body lumen, comprising the steps of:

providing a tubular balloon sheath;

inserting the balloon sheath coaxially between a dilatation balloon and a tubular stent; and inflating the inflation balloon within the sheath so that the sheath constrains the dilatation balloon to a relatively noncompliant inflation profile.

2. The method of claim 1, wherein said balloon sheath comprises at least an inner layer and an outer layer.

3. The method of claim 2, wherein said inner layer comprises an inelastic material, and said outer layer comprises an elastic material.

4. The method of claim 2, wherein said inner layer comprises polyethylene terephthalate.

5. The method of claim 1, wherein the insertion step comprises positioning the dilatation balloon within a partially expanded stent in the lumen, then advancing the balloon sheath distally along the catheter by advancing an axially moveable push wire attached to the sheath until the sheath covers the dilatation balloon.

6. The method of claim 1, wherein said balloon sheath comprises a radiopaque marker.

7. The method of claim 1, wherein a pushwire extends proximally from said balloon sheath, and said inserting step includes axially moving the pushwire.

* * * * *